United States Patent [19]

Dyer et al.

[11] Patent Number: 4,498,345
[45] Date of Patent: Feb. 12, 1985

[54] METHOD FOR MEASURING SAW BLADE FLEXURE

[75] Inventors: Lawrence D. Dyer, Richardson; Anderson D. McGregor, Sherman, both of Tex.

[73] Assignee: Texas Instruments Incorporated, Dallas, Tex.

[21] Appl. No.: 432,619

[22] Filed: Oct. 4, 1982

[51] Int. Cl.³ .................... G01M 5/00; G01N 3/20
[52] U.S. Cl. .................................. 73/849; 73/37; 73/862.45; 83/522
[58] Field of Search .......... 73/862.07, 862.45, 37, 73/837, 849, 780, 807; 83/62.1, 522

[56] References Cited

U.S. PATENT DOCUMENTS 2,728,223  12/1955  Herrman ................. 73/862.45
3,538,765  11/1970  Jesinghaus et al. ..... 73/862.07
3,599,485   8/1971  Muhlberg ............... 73/862.45

FOREIGN PATENT DOCUMENTS 2045284  3/1972  Fed. Rep. of Germany ... 73/862.45

Primary Examiner—Charles A. Ruehl
Attorney, Agent, or Firm—Kenneth C. Hill; N. Rhys Merrett; Melvin Sharp

[57] ABSTRACT

A system for measuring the flexure of a saw blade in situ includes in one embodiment a non-contact displacement sensor and means for directing a fluid flow at the blade adjacent the sensor. The deflection of the blade by the fluid flow is detected by the sensor which generates a signal related to blade flexure. The system indicates when a saw blade is correctly tensioned or when retensioning is required.

1 Claim, 3 Drawing Figures

METHOD FOR MEASURING SAW BLADE FLEXURE

BACKGROUND OF THE INVENTION

This invention relates generally to semiconductor wafer processing and more particularly to the optimization of wafer sawing using an internal diameter saw blade.

In semiconductor wafer preparation the flatness, depth of damage and edge perfection of a wafer are dependent upon the degree to which the internal diameter saw blade follows an ideal plane as it traverses the wafer, and its freedom from out-of-plane vibration. To meet these requirements the saw blade must be kept under a constant, high tension. An improperly tensioned blade will produce bowed or otherwise defective wafers and the useful life of the blade will be diminished, because the blade becomes unstable with respect to deviation under the forces of cutting. Further, the blade becomes free to vibrate with a greater amplitude than a properly tensioned blade.

Methods and apparatus are known in the art for monitoring blade deviation or displacement from a steady-state position as it moves through a crystal. However, these systems do not indicate whether the blade requires retensioning or merely needs dressing. If the blade is dressed when retensioning was the proper course of action, the result will be lower wafer quality and yield.

It is known in the art to measure blade tension by applying a force to the blade rim through a force gauge or a balance arm in contact with the blade and then reading deflection with a dial indicator. This method, however, requires stopping the saw, assembly and calibration of sensitive, precision equipment, and numerous measurements by a skilled operator. This is both expensive and time consuming.

SUMMARY OF THE INVENTION

The present invention provides a rapid, non-contact system and method for measuring blade flexure, and thus blade tension, without demounting the blade and while the blade is rotating. One embodiment of the present invention comprises a non-contact displacement sensor positioned adjacent the cutting rim of the saw blade, and means for directing a fluid flow at the blade near the sensor location. The fluid flow, for example, pressurized air, causes the blade to deflect. The deflection of the blade from its normal or steady-state position is detected by the sensor which produces a signal responsive thereto corresponding to blade flexure. The measured flexure, when compared to the flexure of a properly tensioned blade, is used to indicate when retensioning is required.

It is therefore an object of the present invention to provide an improved system and method for measuring saw blade flexure.

Another object of this invention is to provide a rapid, non-contact system and method for measuring saw blade tension.

Yet another object of this invention is to provide a system and method for in situ measurement of saw blade flexure while the blade is rotating.

BRIEF DESCRIPTION OF THE DRAWINGS

The novel features believed characteristic of the invention are set forth in the appended claims. The invention itself, however, as well as further objects and advantages thereof, will be best understood by reference to the following detailed description of an illustrative embodiment, when read in conjunction with the accompanying drawins in which like numerals represent like parts throughout the several views, and wherein:

DETAILED DESCRIPTION OF THE INVENTION

Figure 1:
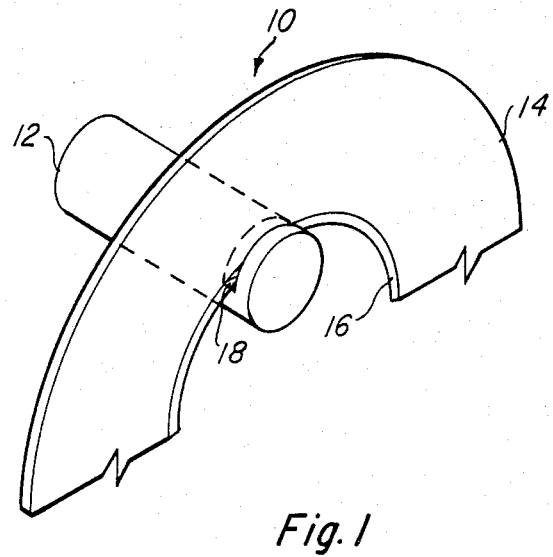
FIG. 1 is a diagrammatic view of a portion of an internal diameter saw blade.

Referring now to the drawings, there is shown in FIG. 1 an internal diameter saw blade 10 for cutting wafers from a semiconductor crystal 12. The core 14 of a typical blade 10 has a thickness of about 4–5 mils. A cutting edge 16 on the inner portion of blade 10 has a thickness of about 10–11 mils and comprises, for example, diamond or other abrasive particles bonded to the blade. A properly tensioned and dressed blade 10 will cut a kerf slot 18 of about 12 mils as it passes through crystal 12. As blade 10 loses tension through normal usage, the flexure, i.e., the distance the blade deflects under a given force, increases and allows the blade to vibrate. It is apparent that as the lateral vibration amplitude increases the kerf slot 18 widens, which correspondingly decreases the yield or the number of wafers that can be cut from crystal 12.

Figure 2:
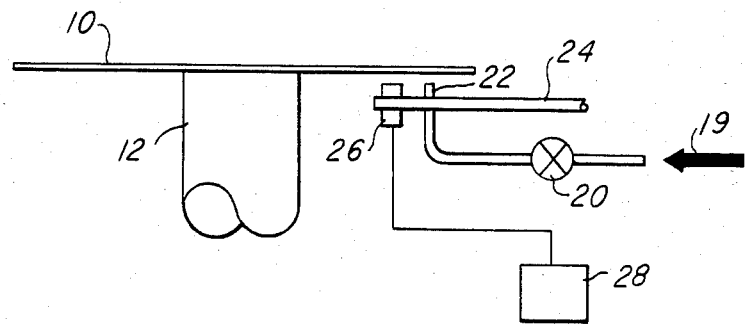
FIG. 2 is a partially schematic plan view of a system according to the present invention.
Figure 3:
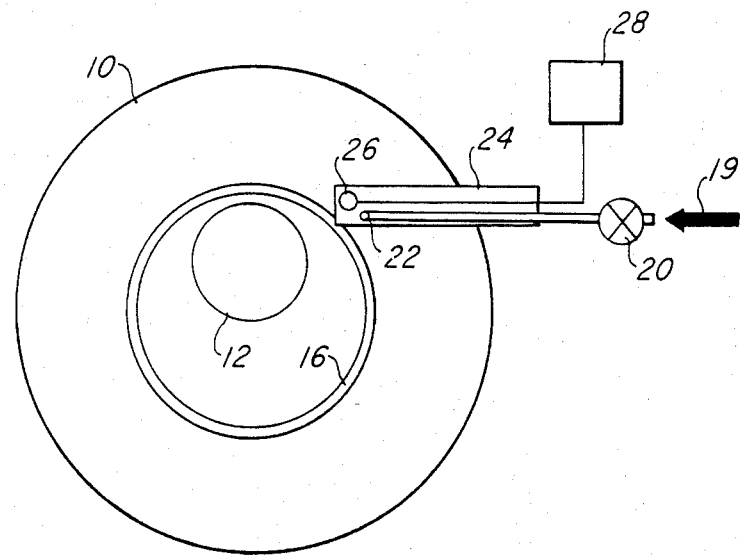
FIG. 3 is an elevational view of the system of FIG. 2.

FIGS. 2 and 3 show one embodiment of a system according to the present invention wherein air (indicated by arrow 19) from a pressurized supply (not shown) is controlled by a valve 20 which is conected to a nozzle 22. Nozzle 22 is positioned a fixed distance, for example 30–50 mils, from blade 10 by a support member 24. A displacement sensor 26 is mounted on support member 24 adjacent nozzle 22. The optimum spacing of sensor 26 and nozzle 22 from blade 10 varies according to the available air pressure, the nozzle 22 orifice, the sensitivity of sensor 26, and the blade 10 characteristics.

Sensor 26 is preferably a non-contact sensor that generates an electrical signal related to the lateral displacement of blade 10. This signal is coupled to a meter 28 or other suitable device to provide an indication of blade deflection. Such sensing and indicating devices are known in the art, for example, the "Dyna-Track" system manufactured by Silicon Technology Corporation. With the sensor 26 of this system spaced about 30–50 mils from blade 10, it has been found that at a pressure of about 60 pounds per square inch an air flow through a 60 mil nozzle deflects a typical blade approximately 0.5 mil when the blade is properly tensioned. This deflection is a measure of blade flexure and is inversely related to blade tension. As blade 10 loses tension through usage the flexure, and thus the measured deflection, will increase.

In a manual mode of operation an initial reference measurement is made after blade 10 has been tensioned by opening valve 20 and reading the deflection on meter 28. Subsequent measurements are made at periodic intervals and compared to the reference measurement. Retensioning is required when the measured deflection exceeds a predetermined value corresponding to the minimum permissible blade tension. The present system is also advantageously employed during the retensioning operation to determine when the proper tension settings are attained, for example, by obtaining a reading equal to the reference value.

It will be readily apparent to those skilled in the art that above described system may be automated by including means to initiate a measurement at periodic intervals. For example, valve 20 can be opened by a solenoid (not shown) coupled thereto responsive to a signal from a counter which increments after each saw operation. Blade 10 flexure would thus be automatically measured each time a preselected number of wafers are cut. Means may also be included to provide an alarm indication when the tension lower limit is exceeded, or to disable the saw until corrective action is taken.

The present invention therefore provides a system for rapidly measuring saw blade flexure while the blade is installed and rotating. The system may readily be automated for periodically measuring the blade flexure and providing an indication when the blade tension falls below acceptable limits.

While the present invention has been described and illustrated with respect to specific embodiments, it is to be understood that various modifications may be made without departing from the spirit and the scope of the invention.

What is claimed is:

1. A method for measuring the flexure of an internal diameter saw blade suitable for slicing wafers from a semiconductor crystal, comprising the steps of:

positioning sensor means adjacent the cutting edge of the saw blade for generating an output signal proportional to the the displacement of the blade in a direction normal to the plane of the blade;

directing a stream of air at the saw blade adjacent the sensor, while the saw blade is rotating, to displace the blade from its steady state position;

measuring the deflection of the saw blade by measuring the change in the sensor output, wherein the flexure of the saw blade can be determined; and periodically repeating said directing and measuring steps to determine whether the blade flexure falls within a predetermined limit.

* * * * *